US008623613B2

(12) United States Patent
Weisenthal

(10) Patent No.: US 8,623,613 B2
(45) Date of Patent: Jan. 7, 2014

(54) METHOD TO DETECT ENDOTHELIAL CELL MASSIVE CALCIUM ACCUMULATION DEATH

(76) Inventor: Larry M. Weisenthal, Huntington Beach, CA (US)

( * ) Notice: Subject to any disclaimer, the term of this patent is extended or adjusted under 35 U.S.C. 154(b) by 0 days.

(21) Appl. No.: 13/085,856

(22) Filed: Apr. 13, 2011

(65) Prior Publication Data

US 2011/0275115 A1 Nov. 10, 2011

Related U.S. Application Data

(60) Provisional application No. 61/323,768, filed on Apr. 13, 2010, provisional application No. 61/460,723, filed on Jan. 7, 2011, provisional application No. 61/465,589, filed on Mar. 22, 2011.

(51) Int. Cl.
*C12Q 1/06* (2006.01)
*C12Q 1/04* (2006.01)
*G01N 1/30* (2006.01)
*G01N 33/48* (2006.01)

(52) U.S. Cl.
USPC .............................. 435/39; 435/40.5; 435/34

(58) Field of Classification Search
None
See application file for complete search history.

(56) References Cited

U.S. PATENT DOCUMENTS 7,226,755 B1 * 6/2007 Peters et al. ................... 435/21
2004/0171089 A1 * 9/2004 Spruce et al. ................. 435/7.23
2006/0073539 A1 * 4/2006 Wikswo et al. ................. 435/29
2007/0190648 A1 8/2007 Weisenthal
2007/0243189 A1 * 10/2007 Yoshizaki et al. ......... 424/133.1

FOREIGN PATENT DOCUMENTS

WO WO-2007/075440 7/2007
WO WO2007075440 * 7/2007
WO WO-2009/143478 11/2009

OTHER PUBLICATIONS

Cao, Yihai. "Antiangiogenic cancer therapy" Seminars in Cancer Biology 14 (2004) 139-145.*
Sueishi et al. "Atherosclerosis and Angiogenesis Its Pathophysiological Significance in Humans as Well as in an Animal Model Induced by the Gene Transfer of Vascular Endothelial Growth Factor." Annals New York Academy of Sciences, Apr. 15, 1997; 311-324.*
Escargueil-Blanc et al., Arterioscler. Thromb. Vasc. Biol. (1997) 17:331-339.
Harada-Shiba et al., J. Biol. Chem. (1998) 273:9681-9687.
Ince et al., J. Natl. Cancer Inst. (2005) 97:981-989.
Mason, J. Am. Col. Cardiol. (1999) 34:1857-1866.
Mohler et al., J. Heart Valve Dis. (1999) 8:254-260.
Orrenius et al., Nat. Rev. Mol. Cell Biol. (2003) 4:552-565.
Spyridopoulos et al., Arterioscler. Thromb. Vasc. Biol. (2001) 21:439-444.
Staton et al., Int. J. Exp. Path. (2004) 85:233-248.
Stefanec, Chest (2000) 117:841-854.
Weisenthal et al., ASCO 2008 Breast Cancer Symposium, Washington D.C., Abstract No. 166.
Weisenthal et al., Cancer Res. (1983) 43:258-264.
Weisenthal et al., Cancer Res. (1983) 43:749-757.

(Continued)

*Primary Examiner* — Blaine Lankford, Jr.
*Assistant Examiner* — Lauren K Van Buren
(74) *Attorney, Agent, or Firm* — Morrison & Foerster LLP

(57) ABSTRACT

Stains that are specific for calcium ion are used to assess and predict the effects of various treatments on the viability of cell types contained in a sample, wherein said stain detects endothelial cells that have massive calcium accumulation death.

23 Claims, 9 Drawing Sheets

Cells in Microcluster

(56) References Cited

OTHER PUBLICATIONS

Weisenthal et al., J. Clin. Oncol. (2010) 28(Supp.):Abstract E13617.
Weisenthal et al., J. Intern. Med. (2008) 264:275-287.
Weisenthal et al., Nature Proceedings (2010) at HDL.handle.net/10101/npre.2010.4499.1.
Willet et al., Nature Med. (2004) 10:145-147.
Supplementary European Search Report for EP 11 76 9535, mailed Jul. 18, 2013, 2 pages.
Weisenthal et al., "Death of human tumor endothelial cells in vitro through probable calcium-associated mechanism induced by bevacizumab and detected via a novel method," Nature Precedings (2012), pp. 1-9, retrieved from the Internet.

* cited by examiner

Cells in Microcluster

Negative Control

Fig. 2A
Fig. 2B
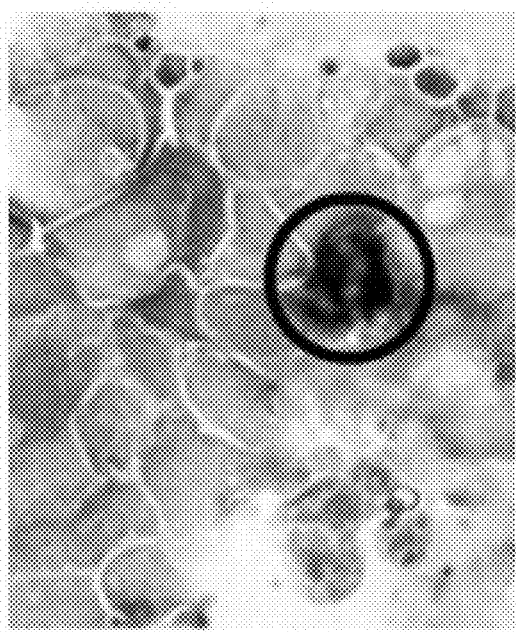
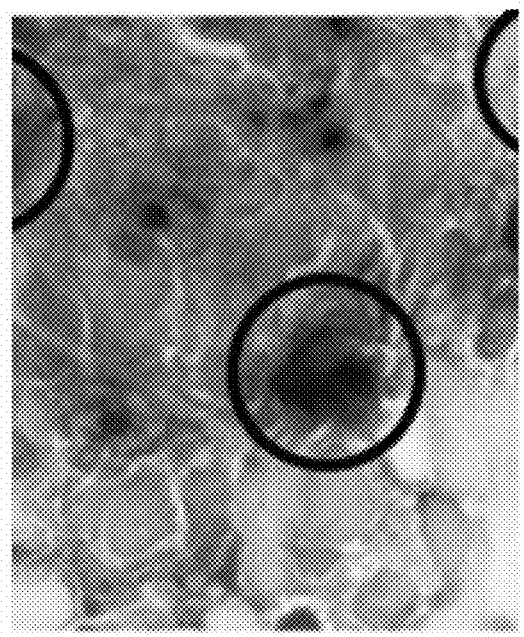
SCLC	Astrocytoma

Fig. 2C
Fig. 2D
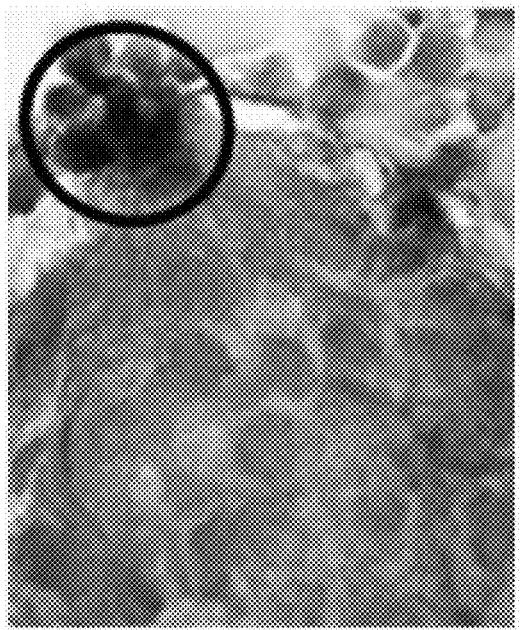

Fig. 2E
Fig. 2F
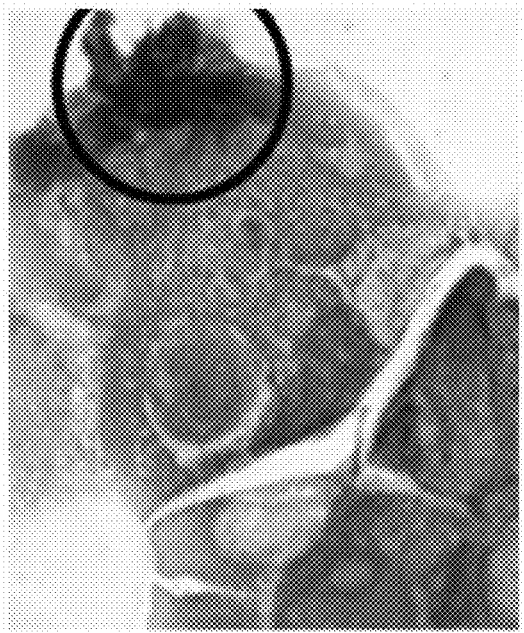
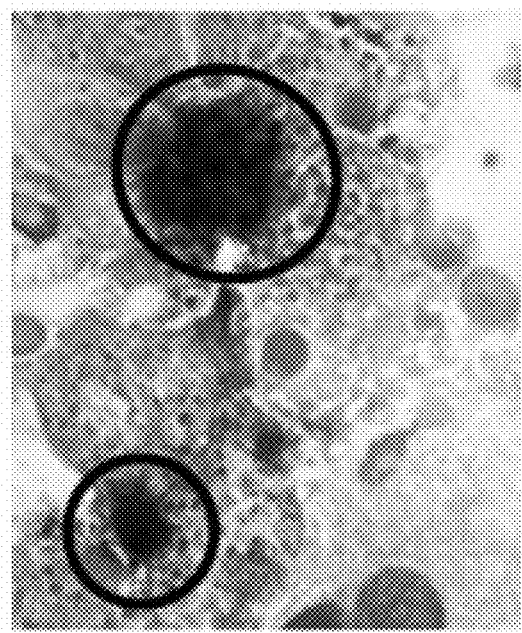

Fig. 2G
Fig. 2H
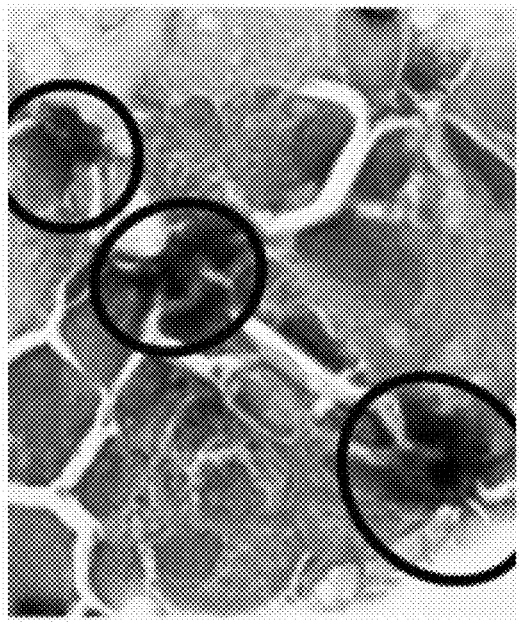
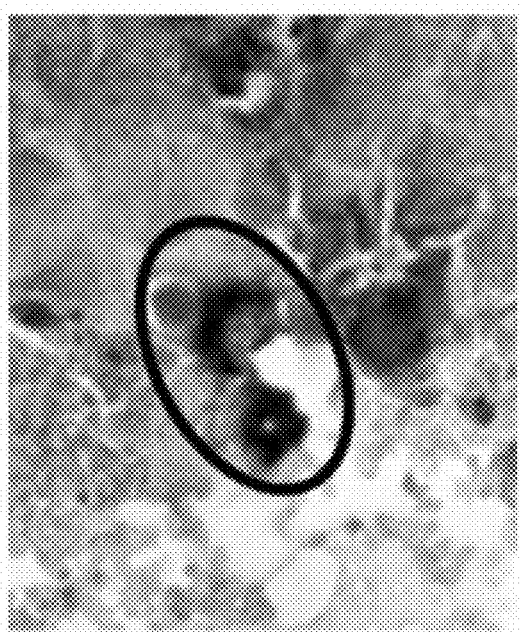
Ovarian
Gall Bladder

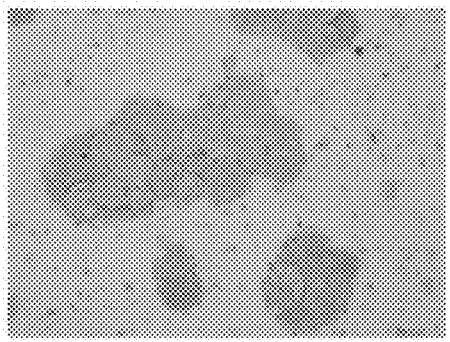
Fig. 3A  Bladder Cancer Control 40X
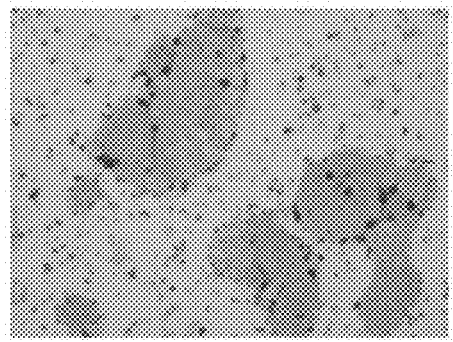
Fig. 3B  Bladder Cancer Avastin 40X
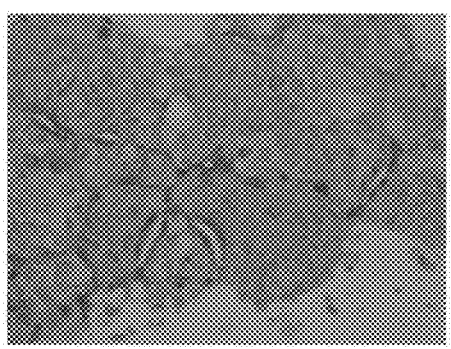
Fig. 3C  Bladder Cancer Control 100X
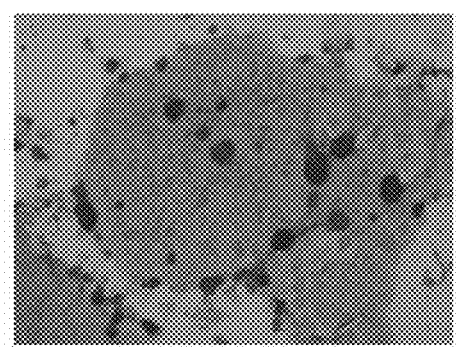
Fig. 3D  Bladder Cancer Avastin 100X
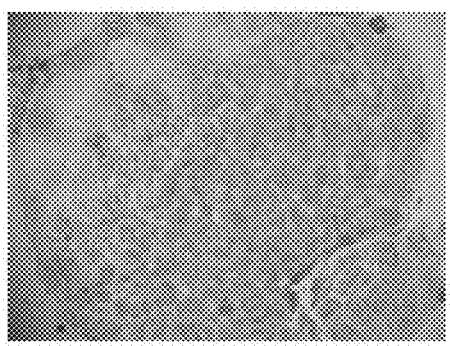
Fig. 3E  Bladder Cancer Control 200X
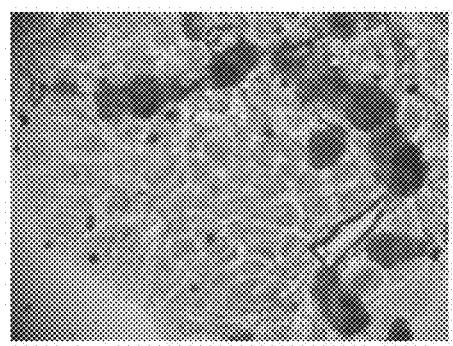
Fig. 3F  Bladder Cancer Avastin 200X

METHOD TO DETECT ENDOTHELIAL CELL MASSIVE CALCIUM ACCUMULATION DEATH

CROSS-REFERENCE TO RELATED APPLICATIONS

This application claims priority from provisional application 61/323,768 filed 13 Apr. 2010, provisional application 61/460,723 filed 7 Jan. 2011 and provisional application Ser. No. 61/465,589 filed 22 Mar. 2011 (entitled "APPROACH FOR TREATING AND PREVENTING ATHEROSCLEROSIS BASED ON BLOCKING MASSIVE ACCUMULATION OF CALCIUM IN ENDOTHELIAL CELLS" filed by Larry M. WEISENTHAL). The contents of these documents are incorporated herein by reference in their entirety.

TECHNICAL FIELD

The present invention relates to implications and applications of a type of apoptosis specific for endothelial cells associated with enhanced levels of calcium ion. This unique form of death, massive calcium accumulation death (MCAD) is a desirable outcome in treating tumors susceptible to antiangiogenic agents and in treatment of retinal neovascularization. Protocols and agents that prevent MCAD are useful in the treatment of or in prevention of diabetic angiopathy and atherosclerosis and heart valve calcification. The invention is useful in assessing the effect of candidate drugs for treatment of tumors, especially those drugs that specifically and directly inhibit the growth of neovasculature, as well as identifying protective agents.

BACKGROUND ART

When tissues (normal and neoplastic) increase in size, they require the formation of microcapillaries (angiogenesis) to provide nourishment to sustain their growth. Constituents of these microcapillaries include most prominently endothelial cells, but also associated mesenchymal cells, fibroblasts, smooth muscle cells, and pericytes. Angiogenesis is important in normal processes, such as wound healing, but also in diseases such as cancer, psoriasis, diabetes, rheumatoid arthritis, and age-related macular degeneration.

There is a need for improved methods for studying microcapillaries in vitro in both normal and diseased tissues. A summary of presently known methods is provided in Staton, et al., "Current Methods for Assaying Angiogenesis in vitro and in vivo," *Int J Exp Path* (2004) 85:233-248. In vivo models are useful but cumbersome. In vitro models are less cumbersome but also more artificial and less relevant.

In particular, there is a need for improved methods to predict the activity of anti-cancer drugs and other treatments which target the microvasculature of tumors. For example, bevacizumab (Avastin®) is an FDA-approved anti-cancer drug which targets the microvasculature of tumors. The wholesale cost of Avastin® is more than $40,000 for 10 months of treatment; yet only a relatively small percentage of patients derive substantial benefit. As stated by Ince, et al., "Association of k-ras, b-raf, and p53 Status with the Treatment Effect of Bevacizumab," *J Natl Cancer Inst* (2005) 97:981-989, the identification of biomarkers that may predict which patients are most likely to respond to such treatment is of considerable interest.

The most commonly used in vitro methods involve isolating and culturing endothelial cells. Once the cells have been cultured, the effect of drugs (or other perturbations) may be studied, using a variety of cell proliferation and/or cell death endpoints. Examples of cell proliferation endpoints include radioactive thymidine incorporation, cell counting, BrdU incorporation, and colony formation. Examples of cell death endpoints include measurement of cellular ATP, mitochondrial reduction of MTT, metabolism and intracellular trapping of fluorescein diacetate (and loss thereof), loss of cell membrane integrity by dye exclusion, and more specific measurements of apoptosis, such as TUNEL assay or caspase expression. In some cases, previously-isolated endothelial cells have been co-cultured with previously-isolated other cells, and differential effects of drugs on the different cell populations have been studied.

Other in vitro methods are based on organ cultures. For example, see Staton, et al., supra). These include rat aortic ring, chick aortic arch, porcine carotid artery, placental vein disk, and fetal mouse bone explant.

Non-cell culture, non-organ culture, approaches to studying and predicting the effects of bevacizumab have been disclosed by Ince, et al., *J Natl Cancer Inst* (2005) supra. Ince attempted to correlate k-ras, b-raf, and p53 status with treatment effect of bevacizumab, but concluded that they "did not identify any subgroup of metastatic colorectal cancer patients who were more likely to respond to bevacizumab therapy." In their discussion, Ince, et al., noted that "To date, few studies have assessed the potential utility of biomarkers in predicting which patients are more likely to respond to antiangiogenic therapy in the clinic" and that no markers had been yet found to be predictive of clinical benefit. These authors suggested that "biomarkers which summarize the effects of all angiogenic regulators may better predict patient outcome than the analysis of a single growth factor or signal induction pathway," but did not suggest any in vitro methods for this purpose. Instead, they noted ongoing work in which patients themselves are used as experimental models for predicting their own outcomes.

In these studies bevacizumab (and/or other treatments) are administered to the patient on a trial basis and then "early" treatment effects are assessed by means of external diagnostic scanning (e.g., MRI) and/or post-treatment tumor biopsies, with histopathologic evaluation of treatment effects (e.g., Willett, et al., *Nature Med* (2004) 10:145-147. This approach has many obvious disadvantages, including expense of treatment, exposure of patient to potential toxicity of ultimately ineffective therapy, and the expense of diagnostic studies (e.g., MRI). Such studies also lack of ability to test multiple different treatments simultaneously without risk to the patient as is possible with in vitro methods.

PCT publication WO2007/075440, the work of the applicant herein, describes assessing the effects of treatment on mixtures or microaggregates of endothelial and non-endothelial cells using microscopic observation of absorption of dyes that are rejected by viable cells but taken up by non-viable cells, in particular fast green. The observation was made by the applicant that dead endothelial cells were distinguishable through their appearance from both live and dead tumor cells or non-endothelial cells. This distinction, however, relied on observations that were more readily perceived if the non-endothelial cells themselves were not killed by whatever treatment was administered. In that case, a second indicator dye which is taken up by living cells could be used to contrast living cells from the dead endothelial cells resulting in what was characterized as a blueberry pancake where the dead endothelial cells showed up as "blueberries" against a pink background. Other publications describing this in general, also representing the work of the applicant, include Weisenthal, L. M., et al., *J. Intern. Med.* (2008) 264:275-287;

Weisenthal, L., et al., ASCO 2008 Breast Cancer Symposium, Washington, D.C., Abstract No. 166; and Weisenthal, L, et al., *J. Clin. Oncol.* (2010) 28:Supplement:Abstract E13617.

Even if the non-endothelial cells were killed by the treatment, a distinction could still be made. Only endothelial cells that die have a distinct appearance being refractile, hyperchromatic and blue-black in appearance when stained with Fast Green, whereas any dead non-endothelial cells were a paler blue. In the subsequent PCT publication, also the work of the current applicant, publication number WO2009/143478, advantage was taken of the distinctive appearance of endothelial cells in response to toxic agents specific therefor to detect and quantify circulating endothelial cells as an index of well being. Again, the appearance of these dead endothelial cells permitted this assessment. Using this method, it was also found that sub-toxic blood levels of ethanol and/or DMSO were useful adjuvants to treatment of unwanted neovasculature.

Although the methods described in the above-referenced PCT publications are effective, they are difficult to adapt to high throughput formats since the contrast between endothelial cells and non-endothelial cells is more intense if the non-endothelial cells are not affected by the treatment. The present invention solves this problem by providing a method whereby the endothelial cells that have been negatively affected by a treatment are readily distinguishable from non-endothelial cells, whether or not the non-endothelial cells have been negatively affected themselves. In addition, it has been found that certain agents effect a particular type of cell death on endothelial cells, whereas non-specific endothelial cell death could alto be effected by different, non-specific agents.

The present method relies on use of dyes that are sensitive to calcium ion. The association of calcium ion with endothelial cell death, in particular in the context of endothelial cells associated with tumors, makes possible the new technique. Calcium accumulation has been observed in the cardiovascular system in the past, but not specifically associated with a specific type of endothelial cell death. For example, Spyridopoulos, I., et al., *Arterioscler. Thromb. Vasc. Biol.* (2001) 21:439-444 report that oxysterol-induced apoptosis in human endothelial cells is enhanced by alcohol in a calcium dependent mechanism; blockage of calcium influx abrogated the alcohol-mediated enhancement of this toxicity. It is also known that oxidized LDL's induce massive apoptosis of cultured human endothelial cells in a pathway that is calcium dependent. Inhibition of calcium influx resulted in blocking apoptosis (Escargueil-Blanc, I., et al., *Arterioscler. Thromb. Vasc. Biol.* (1997) 17:331-339). Calcification of cardiac valves is also noted as a pathology in Mohler, E. R., et al., *J. Heart Valve Dis*. (1999) 8:254-260. On the other hand, alternative mechanisms for oxified LDL apoptosis are described by Harada-Shiba, M., et al., *J. Biol. Chem.* (1998) 273:9681-9687.

A review article regarding the relationship of calcium channel blockers to apoptosis in cancer was published by Mason, R. P., *J. Am. Col. Cardiol*. (1999) 34:1857-1866. This article states that both increases and decreases in cellular calcium levels have been shown to promote apoptotic cell death. The role of calcium channel blockers and promoting cancer was adjudged uncertain. A review of endothelial apoptosis is also found in the article by Stefanec, T., *Chest* (2000) 117:841-854. This review lists increased intracellular calcium ion concentration as a pro-apoptotic stimulus for endothelial cells.

In summary, short term calcium accumulation has previously been associated with endothelial apoptosis wherein calcium has been viewed as a messenger in molecular pathways leading to what is observed as non-specific cell death in endothelial cells, as opposed to its being a central pathogenic agent in and of itself. See, for example, Orrenius, S. et al., *Nat Rev Mol Cell Biol* (2003) 4:552-565. It has now been found that the calcium itself may act as a pathogenic agent resulting in dead cells with massive accumulation of calcium and having a crystalline appearance permitting ease of detection and distinction from non-specific cell death.

Thus, there has been no understanding in the art that death of endothelial cells can be associated with a massive rise in intracellular calcium ion. This type of cell death, massive calcium accumulation death (MCAD) is the subject of the present application. This was reported by applicant in the publication Weisenthal, L., et al., *Nature Proceedings* (2010) at HDL.handle.net/10101/npre.2010.4499.1.

DISCLOSURE OF THE INVENTION

There are some conditions which are benefited by the ability to induce MCAD. These are diseases where unwanted or undesired angiogenesis is occurring, such as solid tumors. Other such conditions include retinal or choroidal neovascular disorders which result in loss of vision. In other instances, it is desirable to prevent MCAD that may be occurring in subjects due to endogenous conditions. Such conditions include, for example, atherosclerosis.

Since MCAD is specifically associated with calcium ion elevation, dyes that detect calcium ion can be used to identify and intensify the staining of cells undergoing this type of cell death. Such dyes can distinguish MCAD from other types of apoptosis associated with both non-endothelial and endothelial cells, such as response to generalized poisons, lack of nutrition, or other environmental factors.

The methods of the invention are able to detect and/or quantify changes, e.g., viability changes, in the microvasculature, including that in isolates from biopsied neoplastic or normal tissues, including those in response to chemical, biological, and/or physical treatments. The methods of the invention can also determine the presence or level of endothelial cells in a biological sample, including biological fluids, and can be used in assays to test potential drugs that are protective against MCAD.

The observed microvascular and other cellular changes serve as tests to predict the in vivo activity of tested treatments, and thus, the methods of the invention, while able to detect specific effects on endothelial cells, also permit the observation of effects of the same or concomitantly administered treatment on the surrounding cells. Thus, a particular drug may affect both endothelial cells and the surrounding cells.

These methods may be used to aid in the discovery and/or development of novel or investigational treatments, as well as used to predict the probability of success of a tested treatment, in particular a treatment designed to inhibit angiogenesis, on a subject from which a sample containing cells has been isolated.

In summary, applicant has discovered that one type of death unique to endothelial cells is associated with a high level of intracellular calcium ion. Therefore, histological stains that are specific for calcium ion provide a high level of contrast between endothelial cells undergoing this type of cell death and other cells in a sample.

Thus, in one aspect, the invention is directed to a method to distinguish massive calcium accumulation death (MCAD) from non-specific cell death which method comprises treating a sample that comprises endothelial cells wherein, in said sample, individual cells can be distinguished, with a dye specific for calcium ion and determining the presence, absence or number of cells that are brightly stained with said dye (due to a massive uptake of said dye) as compared to cells that remain not brightly stained, whereby cells that are brightly stained are identified as cells that have undergone MCAD and cells that are not brightly stained are cells that have not undergone MCAD.

In another aspect, the invention is directed to a method to identify agents that effect MCAD which comprises treating the cells in the sample of the foregoing method with said agent and determining whether said agent results in enhanced bright staining of cells in said sample.

In this aspect, the invention is also directed to a method to determine the effect of a treatment on viability of endothelial cells as compared to non-endothelial cells, which method comprises contacting a sample wherein, in said sample, individual cells can be distinguished, comprising at least viable endothelial cells and viable non-endothelial cells with said treatment;

contacting said composition with at least one dye specific for calcium ion;

determining the presence, absence or number of cells brightly stained by said dye;

whereby said enhanced bright staining of endothelial cells indicates that said treatment has a negative affect on the viability of endothelial cells.

Phrased a slightly different way, the invention is directed to a method to identify an agent that specifically effects the death of endothelial cells, which method comprises treating a sample wherein, in said sample, individual cells can be distinguished, comprised of at least viable endothelial cells and viable non-endothelial cells with a candidate agent;

allowing sufficient time for said agent to exert an effect;

treating the sample with a dye that is specific for calcium ion; and determining wherein, in said sample, individual cells can be distinguished, cells brightly stained by said dye;

whereby an agent that results in enhanced bright staining by said dye is identified as an agent that specifically effects the death of endothelial cells.

In still another aspect, the invention is directed to a method to identify agents which are protective against MCAD which method comprises treating a test sample containing endothelial cells wherein, in said sample, individual cells can be distinguished, with an agent known to effect MCAD in the presence of a candidate protective agent and treating a control sample with said drug known to effect MCAD in the absence of said candidate agent, treating both samples with a dye that is specific for calcium ion and comparing the presence, absence or number of cells brightly stained in the test sample with the presence, absence or number of cells brightly stained in the control sample, whereby a diminution of staining in the test sample as compared to the control sample indicates that the candidate agent is protective against MCAD.

The samples employed in the various methods of the invention may be microaggregates, bodily fluids including blood or plasma, or tissue samples. In order to obtain meaningful results, endothelial cells must be included in the samples.

BRIEF DESCRIPTION OF THE DRAWINGS

FIG. 1A shows cells in microcluster: CD31 cytoplasmic staining confirms morphological identification of microcapillary cells in a tumor microcluster. FIG. 1B shows negative control: living cells in culture, not exposed to anti-VEGF drug; intact membranes of undamaged microcapillary cells exclude vital dye; no visible staining. FIG. 1C shows drug exposure (bevacizumab): leaky membranes of dead/dying micro-capillary cells admit vital dye which then extrudes into adjacent spaces during alcohol-based counterstaining; tumor cells are not harmed by anti-VEGF drug.

FIGS. 2A-2H show the results of prior art methods of staining microaggregates prepared from various solid tumors.

FIGS. 3A-3F are photomicrographs at 40×, 100×, and 200× magnification of microaggregates that are untreated or treated with bevacizumab, and stained with Alizarin red.

MODES OF CARRYING OUT THE INVENTION

Figure 1A:
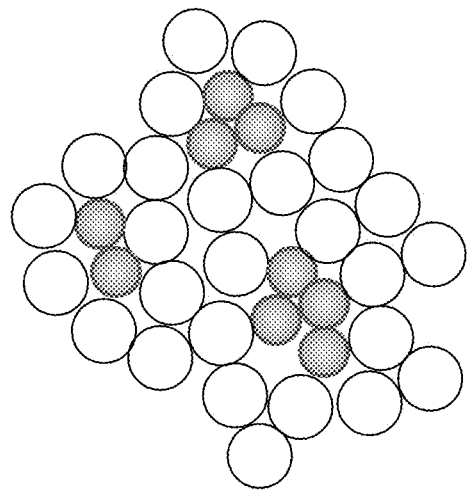
FIGS. 1A-1C are diagrammatic descriptions of the prior art microaggregates useful in some embodiments of the invention.

The invention resides in the discovery that one mode of apoptosis is unique to endothelial cells and is associated with high levels intracellular calcium ion, thus permitting highly specific staining of endothelial cells killed by various treatments. A typical such stain is Alizarin red, but other stains specific for calcium ion such as von Kossa could also be used.

In one embodiment, the invention improves a method set forth in the above-referenced PCT publications WO2007/075440 and WO2009/143478 to study the microvascularity of viable tissue optionally in microaggregates that mimic native conditions or in other samples that contain endothelial cells.

As used herein, "microaggregates" refers to groups of cells that effectively mimic the native environment of the cells being tested therein. In one embodiment, the effect of treatments on endothelial cells is of interest. In this case, the microaggregate will include at least endothelial cells, and sufficient surrounding cells to provide a surrogate for the native environment of said cells. In theory, only one endothelial cell and an accompanying cell might be included. In the present application, "microaggregates", "microclusters", and "clusters" are used interchangeably.

Microaggregates or clusters of cells may be isolated from biopsied tissue. These clusters represent a microcosm of the tissue (tumor or normal) from which the biopsy was obtained, including tumor cells (in the case of cancer), normal tissue cells, connective tissue cells, inflammatory cells, and, in some cases, intact segments of microcapillaries, containing endothelial cells and other cells which are capillary constituents. The clusters may contain as little as one endothelial cell and one non-endothelial cell, but generally several to tens to hundreds to thousands of cells. The clusters may then be cultured in standard tissue and/or organ culture apparatus, in standard tissue/and or organ culture media (containing appropriate nutrients and supplements) for a period of hours to days to weeks. Cells may be exposed to various treatments presumed to have potential effects on the microcapillaries and/or constituent cells of the microcapillaries prior to biopsy (i.e., in the patient), as exhibited in the method of the invention following biopsy, but before cell culture, or during the culture period. Treatments may injure or kill or promote or enhance the survival and/or proliferation of the microcapillaries and/or constituent cells.

Details for preparation of these microaggregates can be found in the above-referenced PCT publication WO2007/075440. In general, the method comprises subjecting a minced biopsy sample to a series of centrifugation steps referred to herein as "quickspin." This is described in more detail below. In each step, the sample is brought to being subjected to a high gravitational force and then immediately allowed to return to 1×g to obtain a cell cluster pellet and a supernatant. The supernatant is removed and the pellet resuspended and the process is repeated until a suitable isolated microaggregate is formed.

The microaggregates can then optionally be cultured or can immediately be sedimented onto a surface for microscopy. Alternatively, the initial preparation of microaggregates can be treated with the $Ca^+$-specific dye, or treatment with the dye can be performed during or after culturing. Staining can be done prior to or after sedimenting the microaggregates onto the surface.

The microaggregates may be cultured in standard tissue and/or organ culture apparatus, in standard tissue/and or organ culture media, containing appropriate nutrients and supplements) for a period of hours to days to weeks. The culturing provides an opportunity to assess the effect of various treatments or factors or protocols on both the endothelial cells contained in the microaggregate and the surrounding cells as well.

Figure 1B:
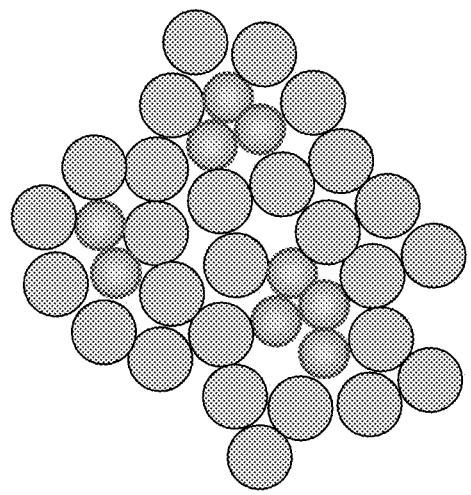
Figure 1C:
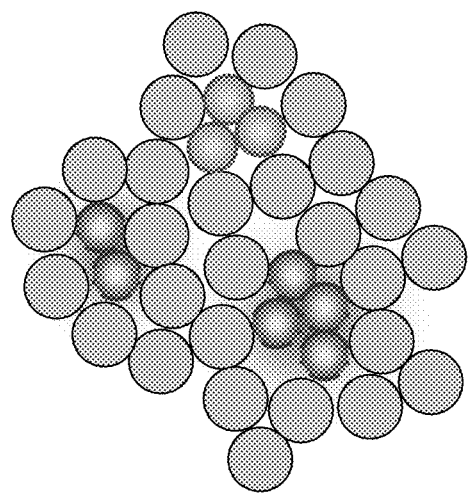

The character of the microaggregates that can be used in the present invention is shown diagrammatically in FIGS. 1A-1C. In each case, a microcluster of cells is shown prepared as described herein from biopsied tissue. In FIG. 1A, endothelial cells are confirmed present by staining with CD31 and these cells are shown as shaded surrounded by accompanying cells shown as open circles. In the illustrative diagrams of FIGS. 1A-1C, the intended treatment is exposure to an anti-VEGF drug. FIG. 1B shows a negative control where no treatment was supplied, and as shown, when this cluster is exposed to a dye Catspecific, no change in appearance occurs, since the cells have not been damaged. However, in FIG. 1C, where the cluster has been exposed to an anti-VEGF drug, the dye stains the endothelial cells and they are therefore identified as affected by the drug. The surrounding cells, shown as open circles, are not stained by the dye and remain the same.

Thus, by preparing the clusters shown, the ability of individual endothelial cells to show a response to the anti-VEGF drug, used for illustration, is demonstrated.

During the culture period, cells may be exposed to various treatments presumed to have potential effects on the microcapillaries and/or constituent cells of the microcapillaries and/or surrounding cells. Treatments may be studied that injure or kill the relevant observed cells or treatments may be studied that promote or enhance the survival and/or proliferation of the microcapillaries and/or constituent cells.

Either or both normal tissues and tumor tissues are tested by the invention method, with drug or other treatment effects may be differentially determined on capillary associated (endothelial) cells versus other cells present in the clusters.

The viability of the various cells could also be determined shortly after biopsy without a period of cell culture. Capillary and other cell viability could be measured, for example, in patients who had received no treatment, or in patients who had received clinical treatment some period of time before biopsy (performed with a needle or other biopsy instrument).

While "microaggregates" are a convenient sample for the methods of the invention, other samples can be used. For example, the method can be used simply to determine the number of endothelial cells in bodily fluid as set forth in the above-referenced WO2009/143478. Enhanced levels of circulating endothelial cells may be indicative of abnormal health conditions. Similarly, any sample that contains endothelial cells can be used to assess treatments designed to effect MCAD specifically.

As used herein, "treatment" refers to any deliberate change effected in the environment of the sample. Most commonly, the treatment is adding to a culture of a sample containing at least endothelial cells a pharmaceutical agent, such as a chemotherapeutic drug. However, other treatments might include changes in temperature, pH, culture conditions and composition, such as change in the nutrients supplied, or a combination of various chemical compounds, such as small molecules or peptides. Treatments may also include inclusions of chemokines or any other deliberately administered protocol.

While the foregoing description sets forth in detail the method described in the prior art with the improvement that a dye specific for calcium ion is used instead of, or in addition to, less specific dyes which simply are taken up by dead cells, further aspects of the invention flow from the understanding that the refractive, hyperchromatic appearance of endothelial cells (even when stained with such non-specific dyes) is due to the presence of large amounts of calcium ion. This provides many additional important applications.

First, the invention makes it possible to distinguish, in samples that simply contain endothelial cells (or may contain non-endothelial cells as well), moieties that effect MCAD as opposed to apoptosis caused by non-specific toxic agents. While the fact that MCAD occurs only in endothelial cells makes it possible to distinguish endothelial cell death in general from non-endothelial cell death, endothelial cells themselves are capable of apoptosis both from non-specific toxins or conditions and by virtue of MCAD. Thus, another aspect of the invention relates to simply distinguishing MCAD from non-specific cell death by determining the absorption of a calcium ion-specific dye and the level thereof. Typically, the calcium ion-specific dye will brightly stain cells undergoing MCAD, while faint stains may be obtained from living cells or dead cells not undergoing MCAD due to the low levels of calcium ion ordinarily present. By "bright" staining, is meant that the intensity of the staining is readily observable either by eye, or by quantitatively measuring the absorption of light by cells that have taken up the dye. One may readily compare cells in a sample, wherein only those cells undergoing MCAD show the bright intensity of the staining. Thus, "bright" can be easily determined by a comparison of light absorption by cells undergoing MCAD and those that are not. The "level" of staining is determined by the number of cells within a sample or a defined portion thereof that are brightly stained.

The invention also includes methods to determine drugs or agents that effect MCAD, as opposed to non-specific apoptosis. The method is similar to that conducted on microaggregates described in detail above except that any sample that contains endothelial cells can be used. Thus, bodily fluids, tissue samples in general that contain endothelial cells, or, as illustrated below, cultures of endothelial cell lines such as human umbilical vein endothelial cells (HUVEC) can be used as samples for such determinations.

Determination of treatments that effect MCAD are useful in identifying agents that will effect antiangiogenesis in conditions where angiogenesis is undesirable. Such instances include solid tumors (which require neovasculature for nutrition), macular degeneration which is the result of unwanted neovasculature in the choroid, and any other conditions where neovasculature is undesirable.

Conversely, there are conditions where it is undesirable for MCAD to occur. Notable among these is atherosclerosis where a buildup in calcium in endothelial cells sets in motion a sequence of events resulting in blockage of the blood vessels. As shown below, fats, such as lard, are capable of inducing MCAD. In effect, the massive accumulation of calcium may act as a "burr under a saddle" triggering an inflammatory response in the blood vessel wall which gives rise to a cascade of events leading to atherosclerosis. In these instances, it is useful to find agents that will protect cells against MCAD. This can be done by using comparative cultures or samples one of which (the test sample) contains a protective candidate agent and the other control sample does not. In each case, the samples, which must contain endothelial cells, are treated with a substance known to effect MCAD. In the test culture, if the candidate agent is successful, the protection against MCAD can be determined by demonstrating that the number of cells that are brightly stained by a calcium-specific dye, i.e., the level of staining, is diminished.

Preparation A

Tumor and/or Normal Tissue Specimens

Fresh biopsies or fluid aspirates are obtained from patients with cancer or other illnesses or from normal donors.

Specimens are typically submitted for conduct of the invention method via the anatomic pathology laboratories of the submitting hospitals, or, in some cases, directly from the operating room or a surgeon/physician office. Solid tumor specimens (not exposed to fixatives or frozen) are placed in cold transport medium ($CO_2$-independent medium, InvitroGen/GIBCO, Grand Island, N.Y., supplemented with penicillin/streptomycin, amphotericin B, insulin/selenium/transferrin, and 10% low endotoxin, heat inactivated fetal bovine serum). Specimens are then placed in sturdy Styrofoam shipping boxes, containing 350 gm blocks of "blue ice" frozen to −20° C. These are then shipped either by a priority overnight delivery service or via local land courier. Fluid specimens are mixed well to suspend cell clusters and then poured into sterile 500 ml polypropylene transport bottles. Ten to fifteen units of heparin sulfate are added per ml of fluid submitted.

Copies of the official histopathology reports from the submitting hospitals should be received.

Preparation B

Isolation of Tumor Cell Microaggregates

Solid tumors are minced to pieces smaller than 1 mm (small enough to be aspirated into a standard disposable 10 ml pipette) with high quality curved surgical scissors. Medium in which said tumors may have been transported is reserved, along with the supernatant from the tissue mince. Scissor-minced tumor pieces are digested with collagenase/DNase in RPMI-1640 containing antibiotics and 10% fetal calf serum. Specimens are digested in 50 ml disposable polypropylene centrifuge tubes, assisted by gentle mixing with plastic-coated, magnetic stirring bars over a stirring plate. Specimens are thusly mixed until complete gross digestion has taken place—typically about 2-3 hours for a 1-3 gram specimen. Cytospin™ slides are then prepared from all cell fractions (transport medium, supernatant from tissue mince, and enzyme digestate), and stained with fast green-H/E, as described previously (Weisenthal, et al., "A Novel Dye Exclusion Method for Testing in vitro Chemosensitivity of Human Tumors," *Cancer Res.* (1983) 43:749-757).

Fluid specimens are centrifuged in their entirety to collect all cells in the specimen. Cells are then resuspended in the above RPMI-1640-based medium and cytospins are prepared as described above.

Viable microaggregates are enriched from medium containing a mixture of microclusters that exist in the minced, digested tissue along with single cells, normal cells, red blood cells, dead cells, and debris by means of "quickspins." Quickspins consist of repeated very brief centrifugations at 50-500× g, in which the centrifuge tube is first mixed by moderate hand-shaking, placed in a standard, room temperature, preparatory centrifuge, and then accelerated to the desired speed (determined for each centrifuge by empiric trials) and then immediately turned off once the centrifuge has reached the desired speed and then allowed to coast to a stop. Following each quickspin, the supernatant is aspirated and reserved, while the cell cluster pellet is collected and resuspended for repeated centrifugation steps.

This process is monitored by preparing cytospins of the resuspended cell clusters, until fractions containing 90% of the viable cells as cell clusters are obtained. When it is not possible to achieve this ideal, fractions containing the highest possible percentage of cells in clusters are combined.

The concentrations of cell clusters are adjusted so that approximately 25% of the area of the Cytospin™ cellular "disk" ("spot") is comprised of reddish-pink (viable) tumor cell clusters, and 75% is comprised of empty space. This cell concentration is of critical importance, as overplating and underplating may produce artifactual drug resistance and sensitivity results and/or may adversely affect survival of the cell clusters during subsequent culture. Assay conditions must be standardized, as results are based on comparison with a universe of comparison assays, as described below.

To normalize the results, "day zero" slides are prepared, depicting the condition of the cells not exposed to treatment at the beginning of the assays, and "end culture" slides of negative control (non-exposed cells) are also prepared. So that factors independent of the effect of treatment may be factored out, both day zero and end culture slides are subjectively scored as to (1) percentage of total viable tumor cells (or other cells of interest) which are in clusters (as opposed to being single cells); (2) average density of cell clusters, where "loose" clusters have clear spaces between the cells following Cytospin™ centrifugation, "medium" clusters do not contain clear spaces between cells but are flattened to a two dimensional appearance, and "tight" clusters maintain a three dimensional appearance following Cytospin™ centrifugation, and (3) median two dimensional area of the cell clusters, as measured with an ocular micrometer. These factors all influence the ability of the treatment to reach the relevant cells, so they must be taken into account when comparing results. It may be advantageous to loosen "tight" cultures so as to permit easier penetration by macromolecules, such as antibodies. This can be effected by adding enzymes such as hyaluronidase to the digest. In addition to these cluster measurements, slides are subjectively scored to determine the ratio of viable cells in the end of culture relative to the number of viable cells at the beginning of culture (zero hours or "day 0").

Preparation C

In Situ Microcapillary Viability Assay (ISMCVA)

Comparative Results with Prior Art Staining

On the fourth culture day, 0.010 ml of Alamar Blue dye solution (Trek Diagnostic Systems, Westlake, Ohio) is added to all culture wells in the 96 well culture dish. After 4 hours, absorbencies at 570 mµ and 600 mµ are recorded on a standard microplate reader (Dynatech). Absorbencies at 600 are subtracted from absorbencies at 570 and corresponding readings in the positive control (high concentration cisplatin/anguidine) wells are subtracted from the readings of each drug-exposed well. Each value so determined is divided by the corresponding values from the negative (vehicle) control wells (0.9% NaCl), also with positive control readings subtracted. The above result provides a crude (relatively insensitive) index of drug-induced cell death (for all cells in the culture, not distinguishing between the death of different populations of cells), which is, none-the-less, useful as an additional quality control to ensure that the microplate wells are correctly spun down on correctly-labeled ISMCVA Cytospin™ slides.

Assay Cytospin™ slides are prepared as previously described (Weisenthal, et al., supra (1983)), with the addition of acetaldehyde-fixed duck red blood cells (Weisenthal, et al., "Comparison of Dye Exclusion Assays with a Clonogenic Assay in the Determination of Drug-Induced Cytotoxicity," Cancer Res (1983) 43: 258-264), which, in the present assays, are used primarily as a quality control to gauge the uniformity of Cytospin™ cellular "disks" ("spots"). Post-culture slides are subjectively scored to gauge cell death as follows:

Slides are first inspected to determine which cells and clusters are tumor cells and which, if any, are normal cells, using standard cytopathologic criteria. Particular attention is given to putative capillary-associated cells, which are typically interspersed throughout the clusters and which can be recognized with practice and experience as small, often angulated cells in close proximity to one or more other cells of similar appearance. These cells are quite often somewhat hyperchromatic.

ISMCVA Cytospin™ slide "disks" which have been stained with fast green and H/E are then scored primarily at a magnification of 40×. The slide is scanned to identify cell clusters which are largely viable and with well preserved morphology. Cell clusters should ideally contain a minimum of 20 non-capillary cells.

The negative control (0.9% NaCl vehicle) slides are scanned to determine (mentally) how slides appear in the complete absence of drug effect. The well-preserved negative control cell clusters can be referred to as "plain pancakes," to connote their relatively uniform appearance. Drug exposed cultures are examined, to select well-preserved, largely viable cell clusters. Under low power, the microaggregate is scored as to being either a "plain pancake" (if it is of largely uniform appearance) versus a "blueberry pancake," if there are multiple punctate areas staining blue-green, which, on high power, are found to be consistent with dead (fast green stained) capillary-associated cells. If desired, additional slides can be prepared and stained with an immunocytochemical method capable of specifically identifying capillary associated cells, such as staining for the CD31 antigen which is reasonably specific for endothelial cells.

If a "blueberry pancake" effect is observed in test cultures greater than that appearing in control cultures, this effect may be scored using a subjective, but standardized grading scale, such as "1+ blueberries," "4+ blueberries," etc. Alternatively, a microscope eyepiece grid may be superimposed over the cell clusters of interest, and the number of "blueberries" per grid unit can be counted with the aid of a standard hand tally counter. The "blueberries" could also be scored using automated image analysis systems.

Typical results are shown in FIG. 2 for microaggregates of solid tumors, where the drug is Avastin® (bevacizumab).

The following examples are offered to illustrate but not to limit the invention.

Example 1

Culture/Treatment Step

To test the effect of treatment, such as effect of a drug, the cell cluster suspensions are mixed with 10% (volume/volume) drug solution or vehicle control (most typically 0.9% NaCl). Final volume of cell suspension/drug solution (or vehicle) plated for culture is 0.12 ml. Culturing is in polypropylene round bottom, 96-well culture dishes in a humidified 37° C. incubator for a standardized duration of time.

Stock solutions are generally prepared at ten times the desired concentrations, aliquotted into single-use, 0.5 ml conical polypropylene tubes, and frozen at −70° C. prior to use. Some drugs are maintained at refrigerator temperature, according to manufacturer's recommendations.

Cells are cultured with the index concentration of each drug and, if desired, with dilutions of the index concentration, where the index concentration is determined from training set assays or from the literature. Negative controls generally consist of 0.9% NaCl, and/or the vehicle in which a drug of interest is dissolved. For tumor samples, positive controls are supplied 100 µg/ml of cisplatin plus 1 µg/ml of anguidine (obtained from the National Cancer Institute). Replicate 96-well plates are tested.

Example 2

Bladder Cancer

Specimens of human bladder cancer prepared generally as described in Preparations A and B are treated with Avastin® or are not treated in control specimens. The amount of bevacizumab used is 2.5 mg/ml, which removes all detectable VEGF from the culture medium, thus effecting cell death of endothelial cells that depend on VEGF for growth. The cultures were sedimented onto microscope slides and stained with Alizarin red S and the raw images are shown in FIGS. 3A-F.

As seen from these images, the endothelial cells in the Avastin® treated cultures provide clear images. These raw images were threshold gated to display only the Alizarin red stain features using commercially available ImageJ software. These results are shown in Table 1.

TABLE 1

ImageJ Analysis of Bladder (Transitional Cell) Cancer Depicted in FIGS. 3A-F

| 40X field sampled | Count of individual alizarin-gated features divided by total pixels of cell-gated features (* 10E6) | Area (total pixels) of alizarin-gated features divided by total pixels of cell gated features (* 10E5) |
|---|---|---|
| Avastin ® #1 | 366 | 8629 |
| Avastin ® #2 | 321 | 5353 |
| Avastin ® #3 | 378 | 6663 |
| Avastin ® #4 | 280 | 2859 |
| Avastin ® #5 | 218 | 6262 |
| Avastin ® #6 | 343 | 7292 |
| Mean Avastin ® (95% C.I.) | 318 (218-378) | 6176 (4120-8232) |
| Control # 1 | 59 | 591 |
| Control # 2 | 89 | 644 |
| Control # 3 | 37 | 291 |
| Control # 4 | 48 | 280 |
| Control # 5 | 70 | 575 |
| Control # 6 | 133 | 899 |
| Mean Control (95% C.I.) | 73 (36-109) | 547 (301-791) |
| 2-sided P Student's T | <0.0001 | <0.0001 |

As the imaging software is readily applicable to these specimens, the method is readily adaptable to quantitative high throughput screening.

Example 3

Comparison of Alizarin Staining with Prior Art

Figure 4A:
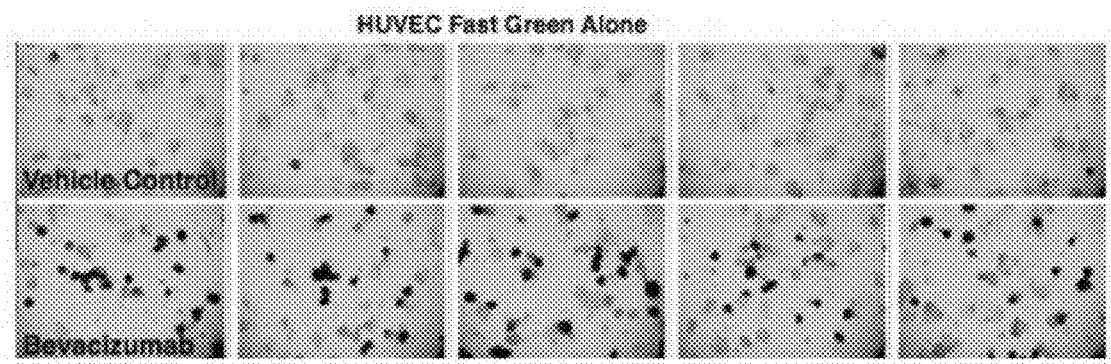
FIG. 4A is a photomicrograph of human umbilical vein endothelial cells (HUVEC) that have been cultured in (unfavorable) anchorage-independent conditions, in the absence (top) or presence (bottom) of bevacizumab. The cells were incubated briefly with fast green dye and sedimented onto a Cytospin™ centrifuge slide according to the prior art method.

Human umbilical vein endothelial cells (HUVEC) were cultured in (unfavorable) anchorage-independent conditions, in the absence or presence of bevacizumab, incubated briefly with fast green dye and sedimented onto a Cytospin™ centrifuge slide. As shown in FIG. 4A, which is a series of photomicrographs of slides prepared as described in this example, fast green dye stains dead cells a pale blue-green, but stains dead cells treated with bevacizumab with massive calcium accumulation a densely refractile blue black, as previously described.

Figure 4B:
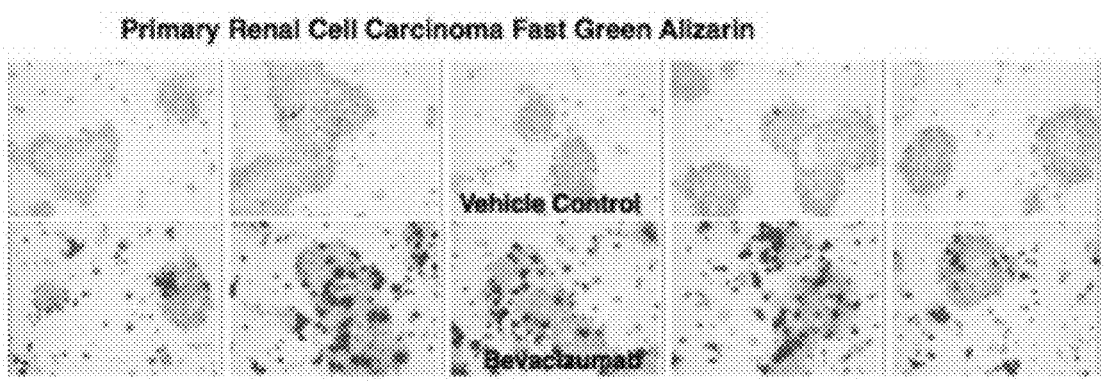
FIG. 4B is a photomicrograph of microclusters of human renal carcinoma cells that have been cultured in the absence (top) or presence (bottom) of bevacizumab. The cells were incubated briefly with fast green dye and sedimented onto a Cytospin™ centrifuge slide, then counterstained with alizarin red s.

Microclusters of human renal carcinoma cells, were cultured in the absence or presence of bevacizumab, incubated briefly with fast green dye and sedimented onto a Cytospin™ centrifuge slide, and then counterstained with alizarin red s, a relatively specific stain for calcium. FIG. 4B shows photomicrographs of several slides demonstrating the intensity and sensitivity of staining with alizarin. Fast green dye stains "non-specifically" dead cells a pale blue-green which is largely, but not completely bleached out in the process of alizarin counterstaining. Alizarin stains viable cells a pale pink (as all viable cells contain small amounts of calcium) but stains dead cells with massive calcium accumulation a densely refractile orange red.

Example 4

Effect of Various Agents on Endothelial Cells

Human umbilical vein endothelial cells were cultured in the presence or absence of bevacizumab, or doxorubicin, or bevacizumab+doxorubicin. After 72 hours, the cells were stained with fast green and sedimented on microscope slides with a Cytospin™ centrifuge. Endothelial cells with non-specific death (NSD) stain pale blue green and endothelial cells with specific, massive-calcium accumulation death (MCAD) stain densely refractile hyperchromatic blue-black. The number of each type of cell was quantified using image analysis software. To show the comparison of the number of dead cells per field, cells cultured in vehicle alone showed approximately 125 cells exhibiting non-specific cell death and approximately 10 cells showing MCAD. When bevacizumab was present, the number of cells showing non-specific cell death decreased to about 100, but the number of cells per field exhibiting MCAD increased to 35. In the presence of doxorubicin, non-specific cell death occurred in 160 cells per field while the MCAD number dropped to 4. The combination of doxorubicin and bevacizumab resulted in about the same number of non-specific cell deaths as doxorubicin alone but an increased level of MCAD, i.e., to 7 cells. Bevacizumab dramatically increased the number of endothelial cells with MCAD, while doxorubicin decreased the number of cells with MCAD and increased the number of cells with NSD. The presence of doxorubicin inhibited the ability of bevacizumab to produce MCAD. It may thus be disadvantageous to administer certain types of conventional chemotherapy drugs along with bevacizumab.

Example 5

Effect of Various Agents on MCAD

Figure 5:
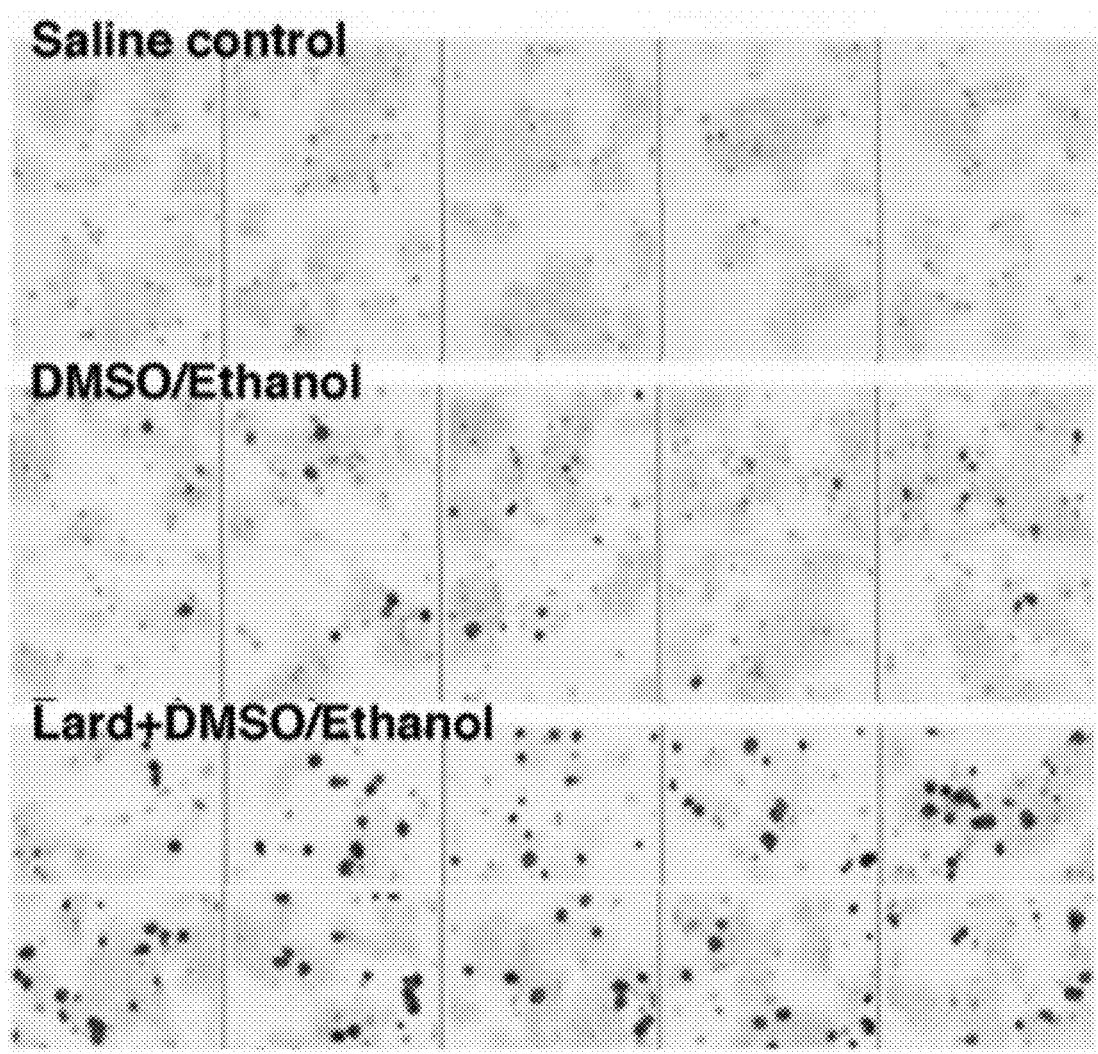
FIG. 5 is a series of photomicrographs of a pure culture of endothelial cells (HUVEC), cultured for 72 hours in the presence of vehicles (saline, or 50% DMSO/50% ethanol) or 50% DMSO/50% ethanol plus lard (1 mg/ml), and treated with fast green dye, sedimented onto microscope slides using a Cytospin™ centrifuge and counterstained with Alizarin red s.

HUVEC cells were cultured for 72 hours in the presence of lard (1 mg/ml, dissolved in 0.5% DMSO+0.5% ethanol) or with 0.9% NaCl ("saline vehicle"), or with 50% ethanol or 50% DMSO or 50% DMSO/50% ethanol. The cells were then treated with fast green, sedimented onto microscope slides using a Cytospin™ centrifuge and counterstained with alizarin red s. As shown in FIG. 5, which depicts a series of photomicrographs of the microscope slides, lard dissolved in the DMSO/ethanol vehicle produced significantly more MCAD than saline vehicle, ethanol alone, DMSO alone, or DMSO plus ethanol.

On a scale where MCAD caused by lard is 1200, the values for DMSO-EtOH, 50% DMSO and 50% EtOH are all less than 500. Saline vehicle shows no MCAD at all.

Exposure of human endothelial cells to toxic lipids produces massive levels of calcium accumulation sufficient to form complex structures containing calcium precipitate, along with degenerating endothelial cells and probably associated toxic lipid. These calcium/degenerating cell/lipid structures comprise a central nidus of vascular inflammation and blocking, and may be initial event(s) leading to atherosclerosis.

The invention claimed is:

1. A method to distinguish massive calcium accumulation death (MCAD) in a sample of dead endothelial cells from nonspecific apoptosis in said dead endothelial cells, which method comprises contacting a sample containing dead endothelial cells with at least one dye specific for calcium ions which allows for individual cells to be distinguished, identifying endothelial cells that are at least 10 fold brighter stained with said dye as compared to cells that are not brightly stained; whereby the cells that are at least 10 fold brighter with said dye indicates the cell death of these cells by MCAD and those that are not brightly stained have not undergone MCAD.

2. The method of claim 1, wherein the sample contains only endothelial cells.

3. The method of claim 1, wherein the sample contains both endothelial cells and non-endothelial cells.

4. The method of claim 1, wherein the sample is in the form of a microaggregate.

5. The method of claim 1, wherein said method includes sedimenting said cells onto a surface for microscopic determination.

6. A method to determine the ability of a treatment to induce massive calcium accumulation death (MCAD) in endothelial cells, which method comprises contacting a sample comprising at least viable endothelial cells with said treatment; contacting said sample with at least one dye specific for calcium ions which allows individual cells to be distinguished; observing the number of dead endothelial cells that are at least 10 fold brighter stained with said dye compared to cells not undergoing MCAD, wherein in said sample, an increased number of individual dead endothelial cells that are 10 fold brighter stained with said dye compared to cells not undergoing MCAD indicates that said treatment induces MCAD.

7. The method of claim 6, wherein said sample contains only endothelial cells.

8. The method of claim 6, wherein said sample contains both endothelial cells and non-endothelial cells.

9. The method of claim 6, wherein the sample is a microaggregate.

10. The method of claim 6, wherein said method includes sedimenting said cells onto a surface for microscopic determination.

11. A method to identify an agent that protects endothelial cells from massive calcium accumulation death (MCAD), which method comprises treating a test sample comprised of at least viable endothelial cells with a candidate protective agent and then an agent that induces MCAD; treating a control sample lacking said candidate protective agent with said agent that induces MCAD; treating both the test sample and the control sample with a dye specific for calcium ions which allows the cells to be individually distinguished; comparing the number of individual endothelial cells that are 10 fold brighter in both the test sample and the control sample; whereby a lower level of brightly stained cells in the test sample than in the control sample identifies the candidate agent as a protective agent.

12. The method of claim 11, wherein the sample contains only endothelial cells.

13. The method of claim 11, wherein the sample contains both endothelial cells and non-endothelial cells.

14. The method of claim 11, wherein the sample is in the form of a microaggregate.

15. The method of claim 11, wherein said method includes sedimenting said cells onto a surface for microscopic determination.

16. A method to detect and/or quantify endothelial cells in a sample, which method comprises contacting a sample comprising at least viable endothelial cells in the sample with an agent that induces massive calcium accumulation death (MCAD) and thus kills any endothelial cells in the sample; contacting the sample with at least one dye specific for calcium ions that distinguishes individual endothelial cells; determining the presence, absence, or number of individual dead endothelial cells that are brightly stained at least 10 fold brighter with said dye compared to cells not undergoing MCAD which indicate that they are endothelial cells, thus permitting detection and quantification of endothelial cells in said sample.

17. The method of claim 16, wherein said sample is a circulating bodily fluid.

18. The method of claim 17, wherein the bodily fluid is blood or plasma.

19. The method of claim 11, wherein said agent is protective against atherosclerosis.

20. The method of claim 16, wherein the sample contains only endothelial cells.

21. The method of claim 16, wherein the sample contains both endothelial cells and non-endothelial cells.

22. The method of claim 16, wherein the sample is in the form of a microaggregate.

23. The method of claim 16, wherein said method includes sedimenting said cells onto a surface for microscopic determination.

* * * * *